US012648825B2

(12) United States Patent
Fearon

(10) Patent No.: US 12,648,825 B2
(45) Date of Patent: Jun. 9, 2026

(54) CERVICOTHORACIC MAT

(71) Applicant: Surgical Compass LLC, Ham Lake, MN (US)

(72) Inventor: Shauna Regina Fearon, Ham Lake, MN (US)

(73) Assignee: Surgical Compass LLC, Ham Lake, MN (US)

( * ) Notice: Subject to any disclaimer, the term of this patent is extended or adjusted under 35 U.S.C. 154(b) by 72 days.

(21) Appl. No.: 18/594,473

(22) Filed: Mar. 4, 2024

(65) Prior Publication Data

US 2024/0299115 A1 Sep. 12, 2024

Related U.S. Application Data

(60) Provisional application No. 63/450,507, filed on Mar. 7, 2023.

(51) Int. Cl.
*A61B 50/20* (2016.01)
*A61B 90/00* (2016.01)

(52) U.S. Cl.
CPC .............. *A61B 50/20* (2016.02); *A61B 90/08* (2016.02); *A61B 2090/0813* (2016.02)

(58) Field of Classification Search
CPC .................... A61B 50/20; A61B 90/08; A61B 2090/0813; A61B 46/00; A61B 46/20; A61B 46/23; A41D 13/00; A41D 13/0518; A41D 13/0512
USPC ...................... 128/849, 852; 2/456, 463, 468
See application file for complete search history.

(56) References Cited

U.S. PATENT DOCUMENTS

| | | | |
|---|---|---|---|
| 3,546,643 A | 12/1970 | Virostek | |
| 4,944,311 A | 7/1990 | Eldridge, Jr. et al. | |
| 5,036,866 A * | 8/1991 | Eldrige, Jr. ............ | A61B 46/23 |
| | | | 128/849 |
| 5,059,271 A * | 10/1991 | Taub ...................... | A61B 46/23 |
| | | | 523/105 |
| 2004/0118410 A1 | 6/2004 | Griesbach, III et al. | |
| 2009/0267717 A1 | 10/2009 | Baskett | |
| 2011/0052858 A1* | 3/2011 | Austria .................. | B32B 25/20 |
| | | | 428/77 |
| 2011/0162659 A1* | 7/2011 | Augustine ................. | A61F 7/00 |
| | | | 128/849 |
| 2012/0259795 A1* | 10/2012 | Hammond ............. | G06Q 40/06 |
| | | | 705/36 R |

(Continued)

FOREIGN PATENT DOCUMENTS

| | | |
|---|---|---|
| EP | 1112035 B1 | 3/2010 |
| WO | 2000/048526 A1 | 8/2000 |
| WO | 2016/164962 A1 | 10/2016 |

*Primary Examiner* — Caitlin A Carreiro
(74) *Attorney, Agent, or Firm* — Dicke, Billig & Czaja, PLLC

(57) ABSTRACT

Examples are directed to cervicothoracic mats that include a top surface including a receiving portion configured to receive surgical instruments and an opposite bottom surface configured to contact a patient, a first lateral surface extending from the top surface, a second lateral surface extending from top surface, and a peripheral portion arranged along the perimeter of cervicothoracic mat proximate to at least a sub-portion of the receiving portion, the peripheral portion being maintained in a non-planar configuration and configured to prevent surgical instruments from falling off of the patient.

18 Claims, 10 Drawing Sheets

(56) References Cited

U.S. PATENT DOCUMENTS

2018/0116892 A1\*   5/2018  Kovyarenko  ............. A45F 5/00
2021/0259795 A1\*   8/2021  Floyd  .................... A61B 50/00

\* cited by examiner

CERVICOTHORACIC MAT

CROSS-REFERENCE TO RELATED APPLICATIONS

This application is a claims benefit to U.S. Provisional Patent Application No. 63/450,507, filed on Mar. 7, 2023 which is incorporated herein by reference in its entirety.

BACKGROUND

Surgery is used to treat a variety of diseases and conditions. Typically, surgeons use surgical instruments which have sharp edges or points to make incisions and perform other tasks. Different surgeries require different types of surgical instruments, with particular surgeons having specific preferences. To obtain the intended surgical instrument, the instrument is generally handed off between the surgeon and other members of the surgical team.

BRIEF DESCRIPTION OF THE DRAWINGS

FIGS. 2A-2B illustrate another example cervicothoracic mat, consistent with the present disclosure.

DETAILED DESCRIPTION

Figure 1A:
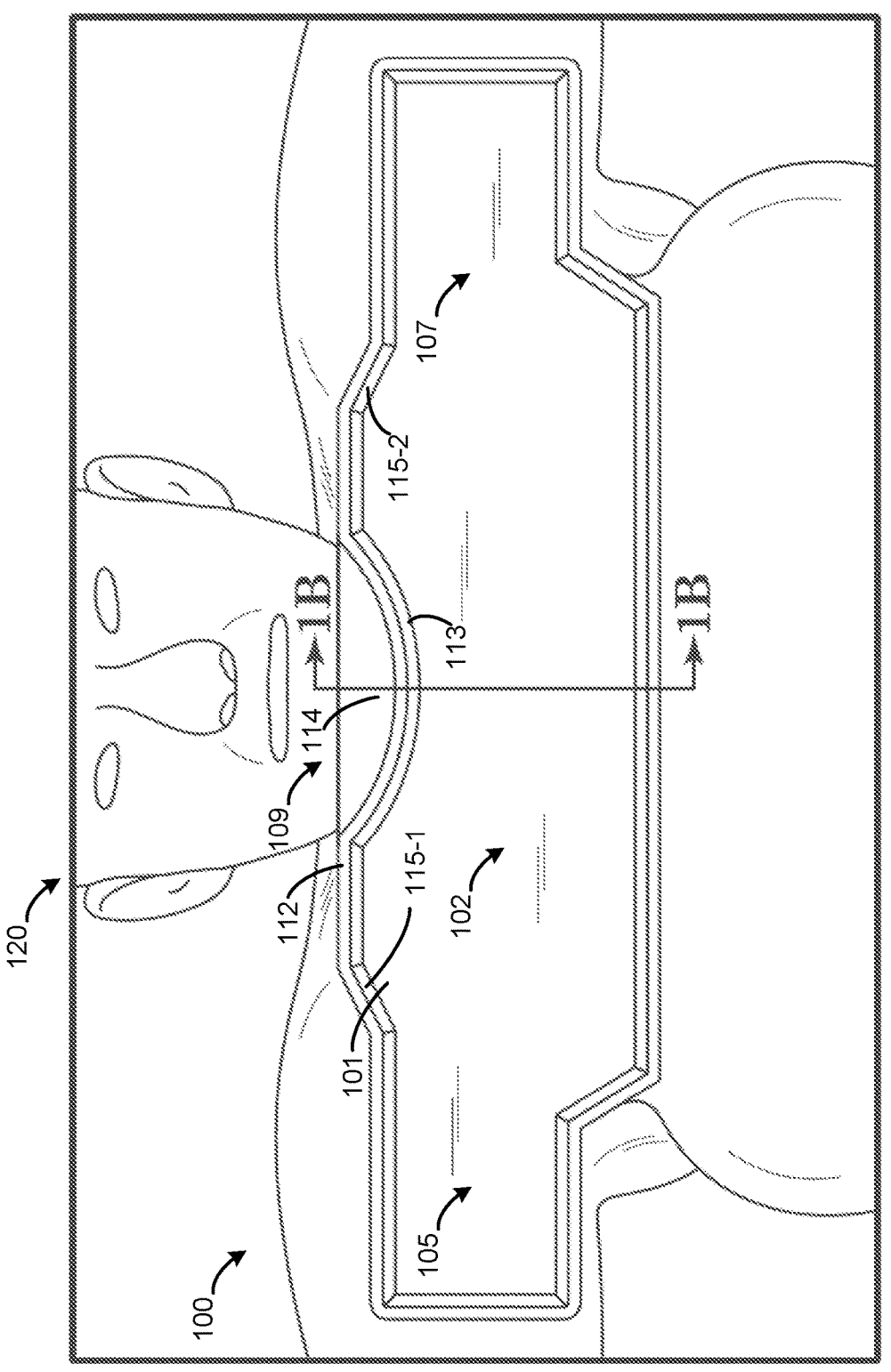
FIGS. 1A-1B illustrate an example cervicothoracic mat, consistent with the present disclosure.

While conducting surgical operations, numerous surgical instruments may be transferred between people, such as surgeons, assistant surgeons, scrub nurses and scrub technicians. Surgical instruments may have sharp protuberances, either for cutting or clasping tissue. Example surgical instruments include suture needles, hypodermic syringe needles, scalpels, wires, retractors, forceps and other instruments.

Traditionally, to transfer surgical instruments between people during surgery, the surgical instruments are handed directly from one person to another. This may involve orienting the surgical instrument in the correct direction so that the person receiving the instrument receives the handle or proximal portion of the instrument rather than the sharp end or distal portion. Even with care taken, sharp injuries are relatively common occurrence when handing off surgical instruments as the person handing over the sharp surgical instrument is at risk from the sharp or distal end of the surgical instrument being closest to them and/or within their hand during the transfer.

Another technique for transferring surgical instruments between people during surgery involves placing the surgical instrument in a tray, such as a kidney dish or other adapted tray, and passing the tray between people. This technique wastes time, which is critical for many types of surgeries, and the person receiving the surgical instrument must still pick up the instrument from the tray without injuring themselves or others or may drop the surgical instrument.

With any of the above-described techniques for transferring surgical instruments during surgery, the techniques require at least one person other than the surgeon to transfer the surgical instruments. In many instances, a surgeon works with different surgical teams (e.g., people) at different times he or she is performing an operation. Members of the surgical team may not be familiar with the way the surgeon works and/or which surgical instruments they use, and/or when and how to pass the surgical instruments to them. This can lead to confusion as to which surgical instrument is required or when, and can slow the surgery time down and/or increase risk of injuries. Furthermore, while it may be proper or required for the surgeon or other personal of the surgical team to hand various surgical instruments back to another person of the surgical team, in the interest of efficiency, convenience and/or for other reasons, in many instances, the surgical instrument may be set down on the patient, such as on the chest or back of the patient and which can increase risk of harm to the patient.

Examples in accordance with the present disclosure are directed to a cervicothoracic mat having a top surface including a receiving portion on which surgical instrument may be rested and an opposite bottom surface which lays on a patient. The cervicothoracic mat further includes a first lateral portion of the top surface that extends from the receiving portion and generally orthogonal from the receiving portion, a second lateral portion of the top surface that extends from the receiving portion and generally orthogonal from the receiving portion, and a peripheral portion arranged along at least a part of the perimeter of the cervicothoracic mat proximate to at least a sub-portion of the receiving portion. The peripheral portion may include or form a ridge that prevents surgical instruments from falling off of the patient when the cervicothoracic mat is placed thereon.

In some examples, the peripheral portion may extend around the entire perimeter of the cervicothoracic mat. In other examples, the peripheral portion extends around a part of the perimeter, and not the entire perimeter of the cervicothoracic mat. In some examples, the peripheral portion(s) include a ridge (e.g., a lip) that is formed where the top surface and bottom surface meet together and/or contact one another. In some examples, such as when the top surface and bottom surface are formed by a common substrate of material, the ridge may include additional material formed along the perimeter. In some examples, the peripheral portion(s) include a least a sub-portion of the top surface. In some examples, the peripheral portion and/or a part of the top surface may include a curved area shape to allow for placement of the chin of the patient. In some examples, the peripheral portion includes a surface that extends from the top surface and the ridge, and that is recessed from the ridge, sometimes herein referred to as "a recessed sub-portion".

Although the above and below described examples include or refer to a cervicothoracic mat and placement on a chest of a patient, examples are not limited. For example, the mat may be placed on the back of the patient or other locations, such as locations that are distal from the cervicothoracic area of the patient.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Figure 1B:
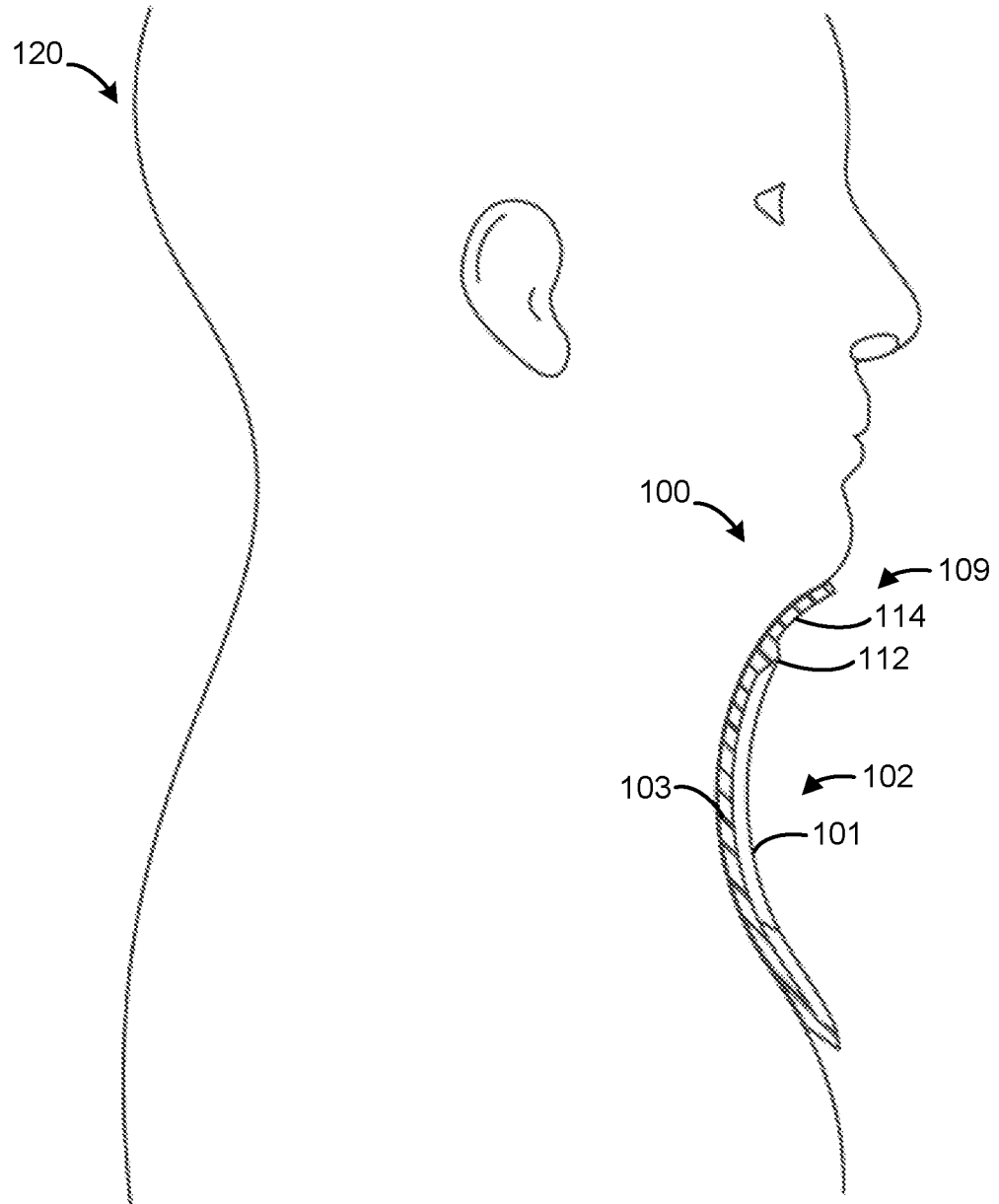

FIGS. 1A-1B illustrate an example cervicothoracic mat for surgical instruments, consistent with the present disclosure.

More particularly, FIG. 1A illustrates a top view of the cervicothoracic mat 100. FIG. 1B is cross-section of the cervicothoracic mat 100 of FIG. 1A along line 1B as illustrated in FIG. 1A. As illustrated in FIGS. 1A-1B, the cervicothoracic mat 100 has a top surface 101 including a receiving portion 102 and an opposite bottom surface 103 configured to contact (e.g., lay on) a patient 120. Surfaces, as used herein, may include and/or refer to material arranged as a substrate and which may provide surface areas.

The top surface 101 and bottom surface 103 may be formed of the same or different materials, such as silicon or other material capable of being sterilized. In some examples, the top surface 101 and bottom surface 103 may be formed of the same piece of material, or different pieces of material which are joined or fused together. As further described herein, the top surface 101 and bottom surface 103 may be formed in a variety of different shapes and may be rester-ilizable to allow for repeated use. In some examples, the top surface 101 and bottom surface 103 and/or the entire cer-vicothoracic mat 100 are formed of a medical grade silicone that may withstand a threshold temperatures from heated surgical instruments (e.g., heat sealing devices, cautery, endoscopes) and/or steam autoclaves. The cervicothoracic mat 100 may be any shape that may fit around or proximate to a surgical area (e.g., surgical site) or sterile field, such as covering the arms, shoulders, neck and at least some the chest, in some examples. Additionally, the cervicothoracic mat 100 may be water proof or water impervious, such that a wet fire towel or other wet objects may be placed thereon.

In various examples, the receiving portion 102 of the top surface 101 is configured to receive surgical instruments. For example, a surgeon or other member of the surgical team may lay a surgical instrument on the receiving portion 102 or other portions of the top surface 101. The receiving portion 102 may include a recessed sub-portion, as further described herein.

The top surface 101 may further include a first lateral portion 105 configured to extend from the receiving portion 102 generally orthogonal from the receiving portion 102 and a second lateral portion 107 configured to extend from the receiving portion 102 and generally orthogonal from the receiving portion 102. In some examples, the receiving portion 102 includes a recessed area disposed between the first lateral portion 105 and the second lateral portion 107. The first and second lateral portions 105, 107 may provide protection to the patient 120, such as portions of the chest, back, and/or arms of the patient. In some examples, the first lateral portion 105 and the second lateral portion 107 are configured to cover a respective portion of the chest of the patient 120, such as when the patient 120 is laying in a supine or prone position with their arms by their sides. In some examples, the first lateral portion 105 and second lateral portion 107 may extend toward an elbow of the patient 120, such as when the patient 120 is laying with their arms extended out.

The cervicothoracic mat 100 further includes a peripheral portion 109 arranged along the perimeter of the cervicotho-racic mat 100 proximate to at least a sub-portion of the receiving portion 102. The peripheral portion 109 is main-tained in a non-planar configuration and configured to prevent surgical instrument(s) from falling off of the patient. In some examples, the peripheral portion 109 comprises a ridge 112 that extends from (e.g., up) the top surface 101 in a direction away from the bottom surface 103. For example, the ridge 112 may be a height in the range of about 2 inches to about a ¼ inch, such as about 1 inch. In some examples, the ridge 112 may be formed by additional material formed along at least a portion of the perimeter of the top surface 101. In some examples, as shown by FIG. 1B, the ridge 112 may be formed by or include a portion of the bottom surface 103 which is thicker than other portions of the bottom surface 103 and which abuts and/or includes a portion of the top surface 101.

In some examples, and as shown by FIGS. 1A-1B, the cervicothoracic mat 100 covers the shoulders of a patient 120 and at least partially covers the chin of the patient 120. As shown by FIG. 1A, the peripheral portion 109 may be configured to receive a chin of the patient 120 and to cover at least a portion of the chin of the patient 120. For example, the peripheral portion 109 may include the ridge 112 and a recessed sub-portion 114 configured to conform to the chin of the patient 120. In some such examples, at least a sub-portion of peripheral portion 109 (e.g., recessed sub-portion 114) is recessed relative to the first lateral portion 105 and the second lateral portion 107.

In some examples, the ridge 112 forms or is a non-planar ridge including a chin curve sub-portion 113 arranged to receive the chin of the patient 120. For example, the non-planar ridge includes angled sub-portions 115-1, 115-2 con-necting the chin curve sub-portion 113 to the first and second lateral portions 105, 107.

In some examples, the cervicothoracic mat 100 may further include a second peripheral portion with angled sub-portions, as further described in connection with FIGS. 2A-2B. In some examples, the peripheral portions (some-times referred to as first and second peripheral portions) may include a ridge 112 which extends around the whole perim-eter of the top surface 101 of the cervicothoracic mat 100, however examples are not so limited.

Cervicothoracic mats, in accordance with various examples, may be used to protect members of the surgical team and/or the patient. In particular, the cervicothoracic mats may provide a location to place the surgical instru-ments without directly handing off between people, thereby reducing or mitigating the amount of times surgical instru-ments are passed between surgical team members and reduc-ing risk of sharp object injuries to both the surgical team and the patient. For many surgeries, different team members of the surgical team are positioned at different locations of the patient. As a non-limiting example, the nurse anesthetist may be located at the head of the operating table proximate to the head of the patient, the surgical technologist may be located on a left side of the patient near the chest of the patient, and the surgeon may be located on the right side of the patient near the chest of patient. Various material may be placed on the patient, such that all team members may not have direct eye sight of one another and/or the parts of the patient. Using the above non-limiting example, towels may be placed around a sterile field (e.g., chest), on the upper chest area, shoulders and neck of the patient, followed by placing draping up, such that the surgeon and surgical technologist may be unable to see the shoulder, face, and neck of the patient, and the nurse anesthetist may be unable to see the sterile field (e.g., chest) of the patient.

Using the above described specific and non-limiting examples, the cervicothoracic mat may be placed proximate to (but not on) the sterile field to provide a location to place the surgical instrument(s) on and thereby increase safety for the patient and the surgical team due to sharp and/or heated surgical instruments, and preventing the surgical instrument(s) from falling into the patient's open surgical cavity and/or onto the floor and being lost and/or damaged. Providing a location to place the surgical instrument(s) may decrease surgical costs and/or complications over time by mitigating lost, broken, and/or contamination of surgical instrument(s) during surgery and/or saving time for the surgeon by allow the surgeon to focus on surgical tasks and to know the location of the surgical instrument(s) and without passing back and forth over the open surgical cavity. Additionally, the cervicothoracic mat may prevent the drapes from starting on fire, by reducing the risk of hot surgical instruments coming in contact with the drape.

Figure 2A:
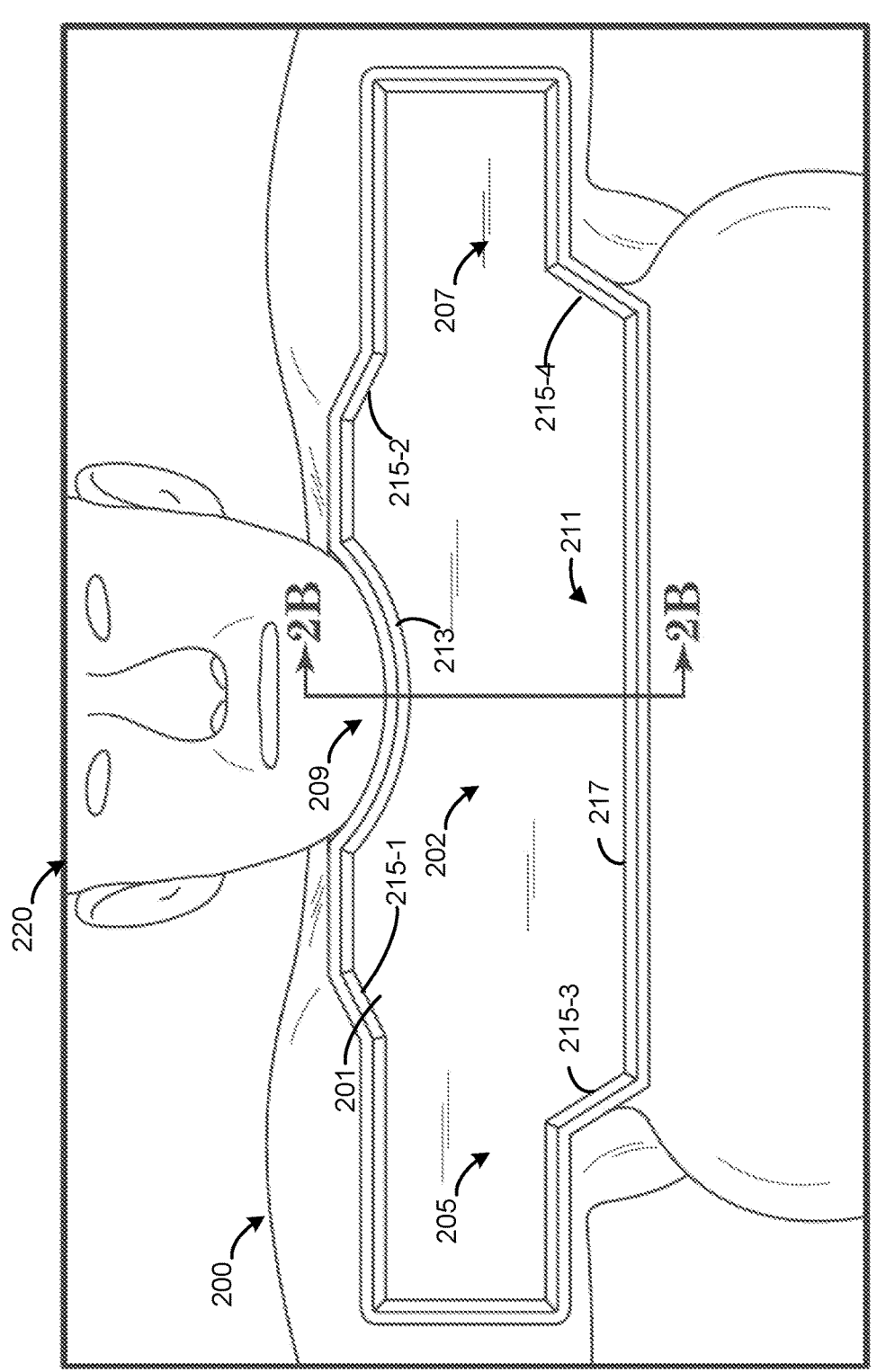
Figure 2B:
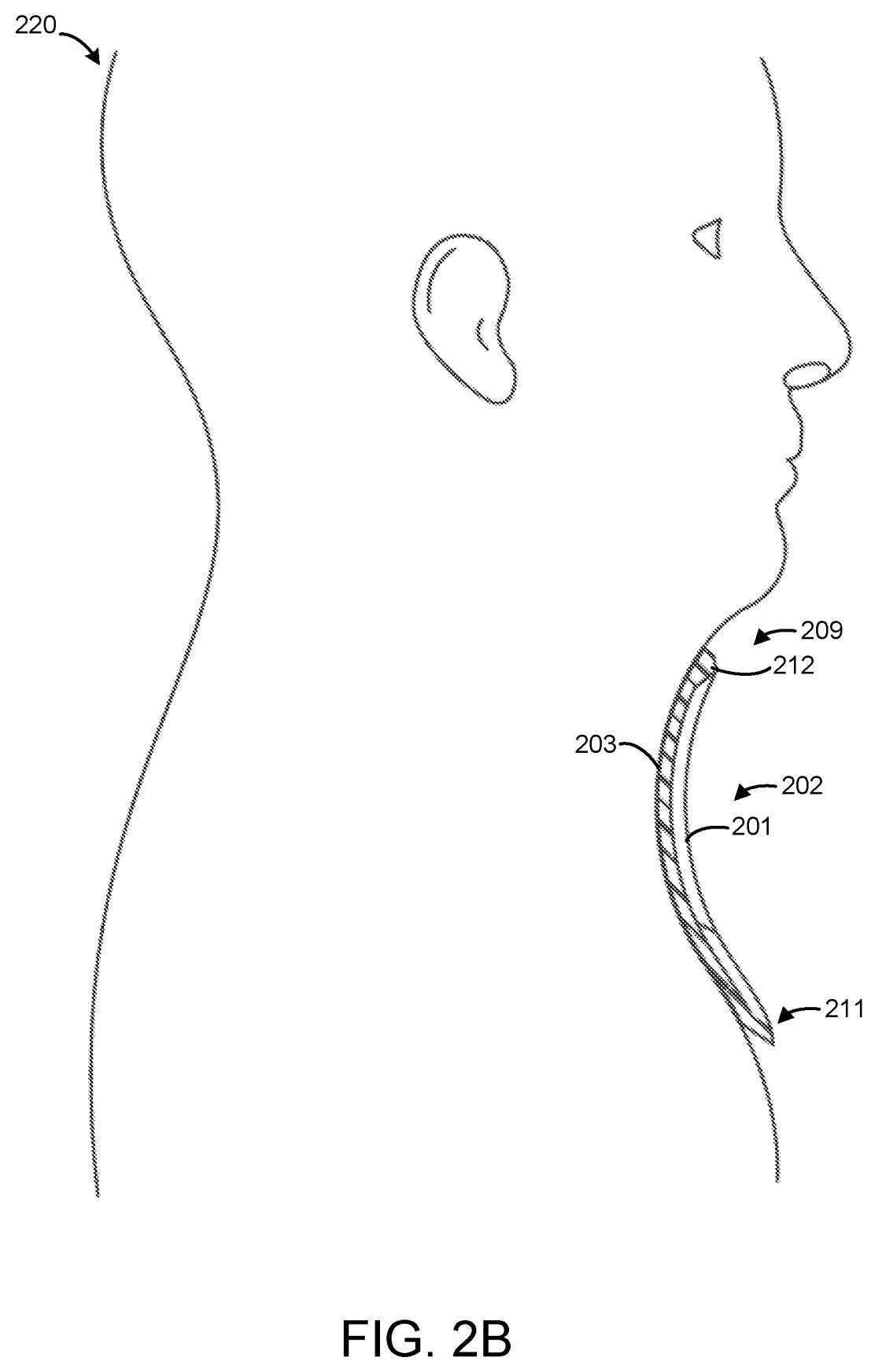

FIGS. 2A-2B illustrate another example cervicothoracic mat, consistent with the present disclosure. The cervicothoracic mat 200 of FIGS. 2A-2B may include at least some of the same features and attributes as the cervicothoracic mat 100 of FIGS. 1A-1B, as illustrated by the similar numbering. For example, the cervicothoracic mat 200 has a top surface 201 including a receiving portion 202 configured to receive surgical instruments and an opposite bottom surface 203 configured to contact (e.g., lay on) a patient 220. The top surface 201 further includes a first lateral portion 205 and a second lateral portion 207 that respectively extend from the receiving portion 202 and generally orthogonal from the receiving portion 202. As with FIGS. 1A-1B, FIG. 2A illustrates a top view of the cervicothoracic mat 100 and FIG. 2B is cross-section of the cervicothoracic mat 200 of FIG. 2A along line 2B.

The cervicothoracic mat 200 further includes a first peripheral portion 209 and a second peripheral portion 211. The first peripheral portion 209 is arranged along the perimeter of the cervicothoracic mat 200 proximate to at least a first sub-portion of the receiving portion 202. In some examples, the first peripheral portion 209 and/or second peripheral portion 211 may not include recessed sub-portions. In some examples, the second peripheral portion 211 is arranged along the perimeter of the cervicothoracic mat 200 and proximate to at least a second sub-portion of the receiving portion 202. The first and second peripheral portions 209, 211 are maintained in a non-planar configuration and configured to prevent surgical instruments from falling off of the patient.

As described above, the peripheral portions 209, 211 may each include or may form a ridge 212. In some examples, peripheral portions 209, 211 may extend around a portion or all of the perimeter of the cervicothoracic mat 200. In some examples, the peripheral portions 209, 211 may include multiple ridges which are separate from one another.

In some examples, as described above, the first peripheral portion 209 forms a non-planar ridge including a chin curve sub-portion 213 and angled sub-portions 215-1, 215-2 that connect the chin curve sub-portion 213 to the first and second lateral portions 205, 207. In some examples, the second peripheral portion 211 includes angled sub-portions 215-3, 215-4 connecting a (lateral or non-curved) sub-portion 217 to the first and second lateral portions 205, 207. In such examples, at least a sub-portion of the second peripheral portion 211 is generally parallel to at least a sub-portion of the first peripheral portion 209. In some examples, the second peripheral portion 211 has or extends a greater length from the receiving portion 202 relative to the first peripheral portion 209.

Cervicothoracic mats in accordance with examples of the present disclosure may include variations from the cervicothoracic mats 100, 200 illustrated by FIGS. 1A-2B. In some examples, the second peripheral portion 211 may include a portion of the top surface 201 that is configured to extend a length of the patient, such as a length of the chest or back of the patient. In some examples, the length may include about 20 inches, although examples are not so limited and may include other lengths and measurements. In some examples, the second peripheral portion 211 may include a projection of the top surface 201 of cervicothoracic mat 200 configured to extend toward a midline of the thoracic region of the patient 220. In some examples, the first and second lateral portions 205, 207 may extend further or less from the receiving portion 202 than illustrated by FIG. 2A. In some examples, the cervicothoracic mats may be other shapes, such as being rectangular, including non-curved perimeters, and other shapes. In some examples, at least the receiving portion 202 or the entire top surface 201 may include a plurality of projections extending therefrom and which are configured to grip surgical instruments when placed on the receiving portion 202. Example projections include fingerlike projections and cross-hatched projections.

FIGS. 3-9 illustrate further example cervicothoracic mats, consistent with the present disclosure.

Figure 3:
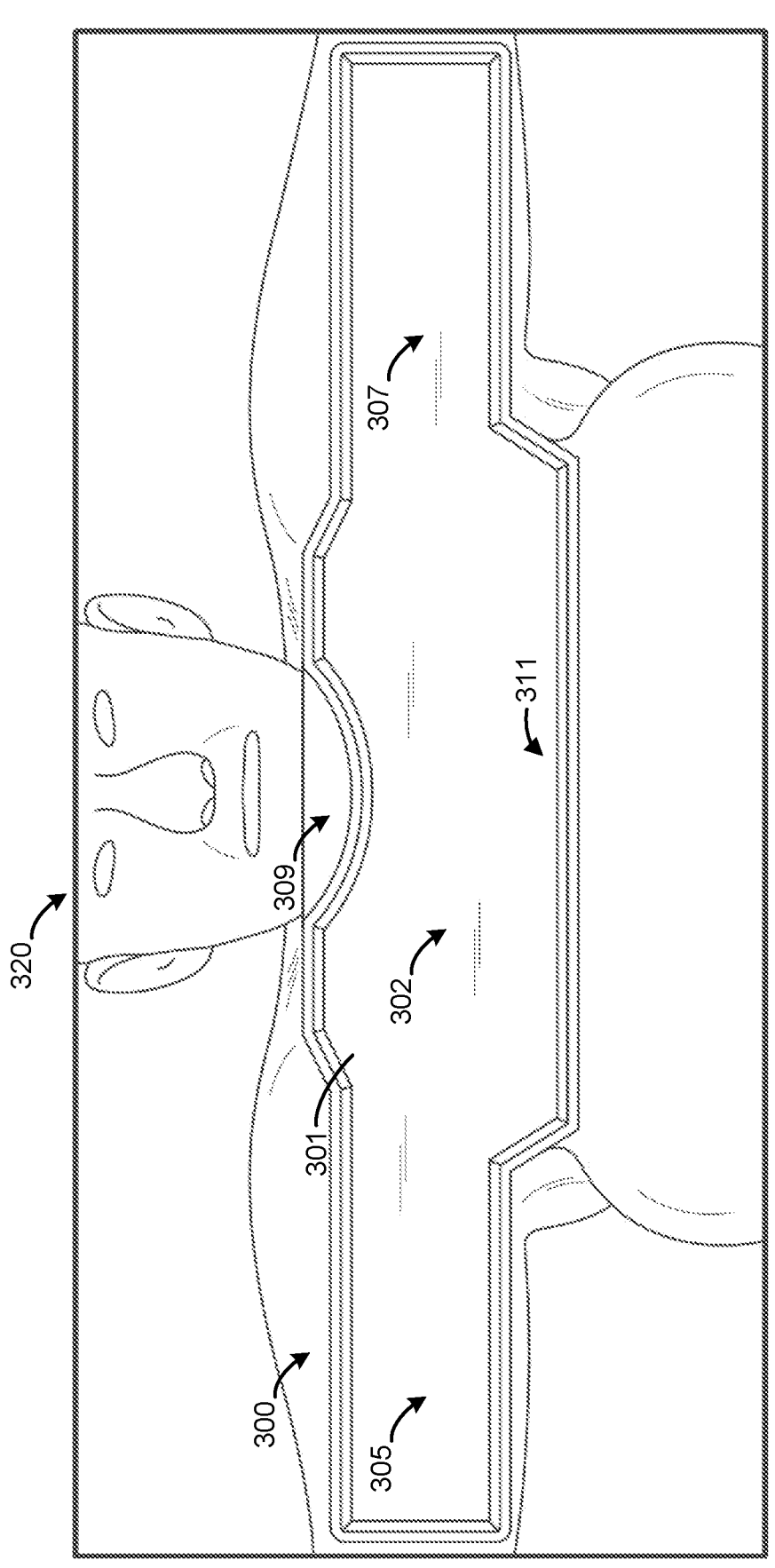
FIGS. 3-9 illustrate further example cervicothoracic mats, consistent with the present disclosure.

FIG. 3 illustrates another example cervicothoracic mat 300 which may include at least some of the same features and attributes as the cervicothoracic mats 100, 200 of FIGS. 1A-2B, as illustrated by the similar numbering. For example, the cervicothoracic mat 300 has a top surface 301 including a receiving portion 302 and an opposite bottom surface (see 103 of FIG. 1B) The top surface 301 further includes a first lateral portion 305 and a second lateral portion 307 that respectively extend from the receiving portion 302. The lateral portions 305, 307 of FIG. 3 extend greater distances from the receiving portion 202 than the lateral portions 105, 107, 205, 207 of FIGS. 1A-2B. The cervicothoracic mat 300 further includes a first peripheral portion 309 and a second peripheral portion 311, as previously described. The lateral portions 305, 307 of FIG. 3 may be useful for surgeries when the patient 320 is in a position with their arms out, and to project the arms of the patient 320.

Figure 4:
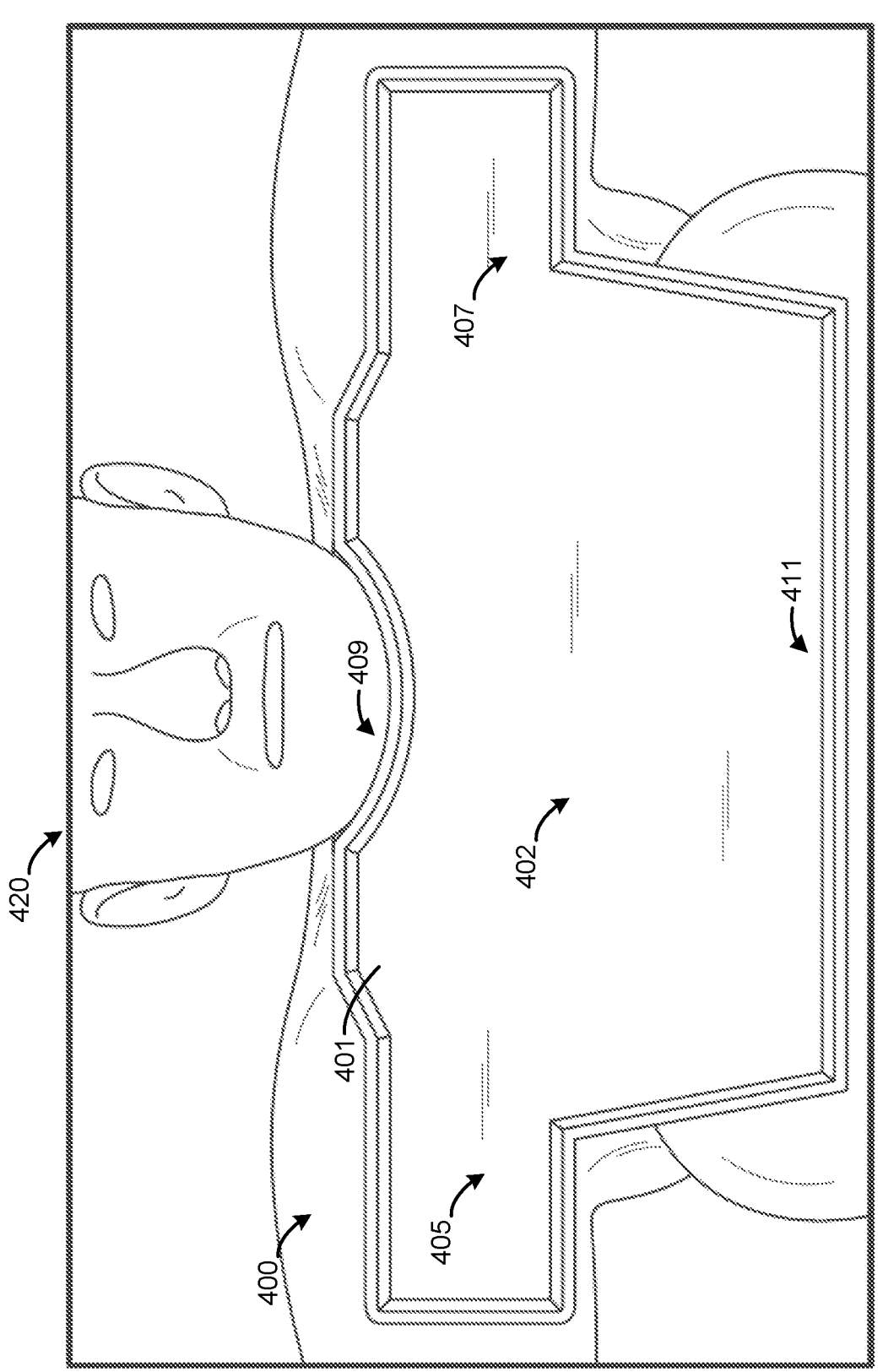

FIG. 4 illustrates another example cervicothoracic mat 400 which may include at least some of the same features and attributes as the cervicothoracic mats 100, 200 of FIGS. 1A-2B, as illustrated by the similar numbering. For example, the cervicothoracic mat 400 has a top surface 401 including a receiving portion 402 and an opposite bottom surface (see 103 of FIG. 1B). The top surface 401 further includes a first lateral portion 405 and a second lateral portion 407 that respectively extend from the receiving portion 402. The cervicothoracic mat 400 further includes a first peripheral portion 409 and a second peripheral portion 411. With cervicothoracic mat 400, the second peripheral portion 411 extends a greater distance from the receiving portion 402 than the second peripheral portions 211 of FIGS. 2A-2B. The second peripheral portion 411 may be useful for surgeries when the patient 420 is laying prone or with their hands by their side and to provide protection to the chest, back, and/or other surfaces of the patient.

Figure 5:
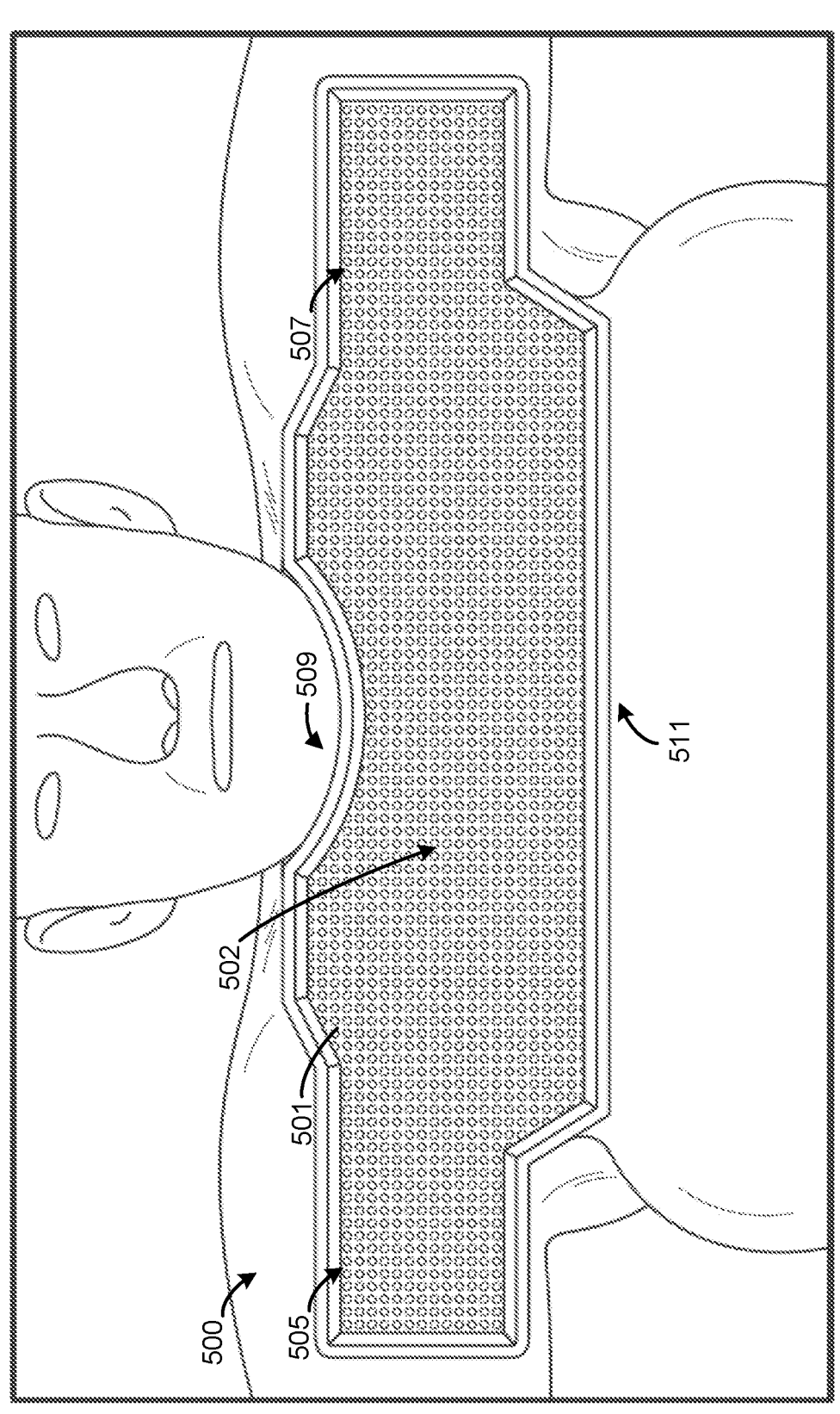
Figure 6:
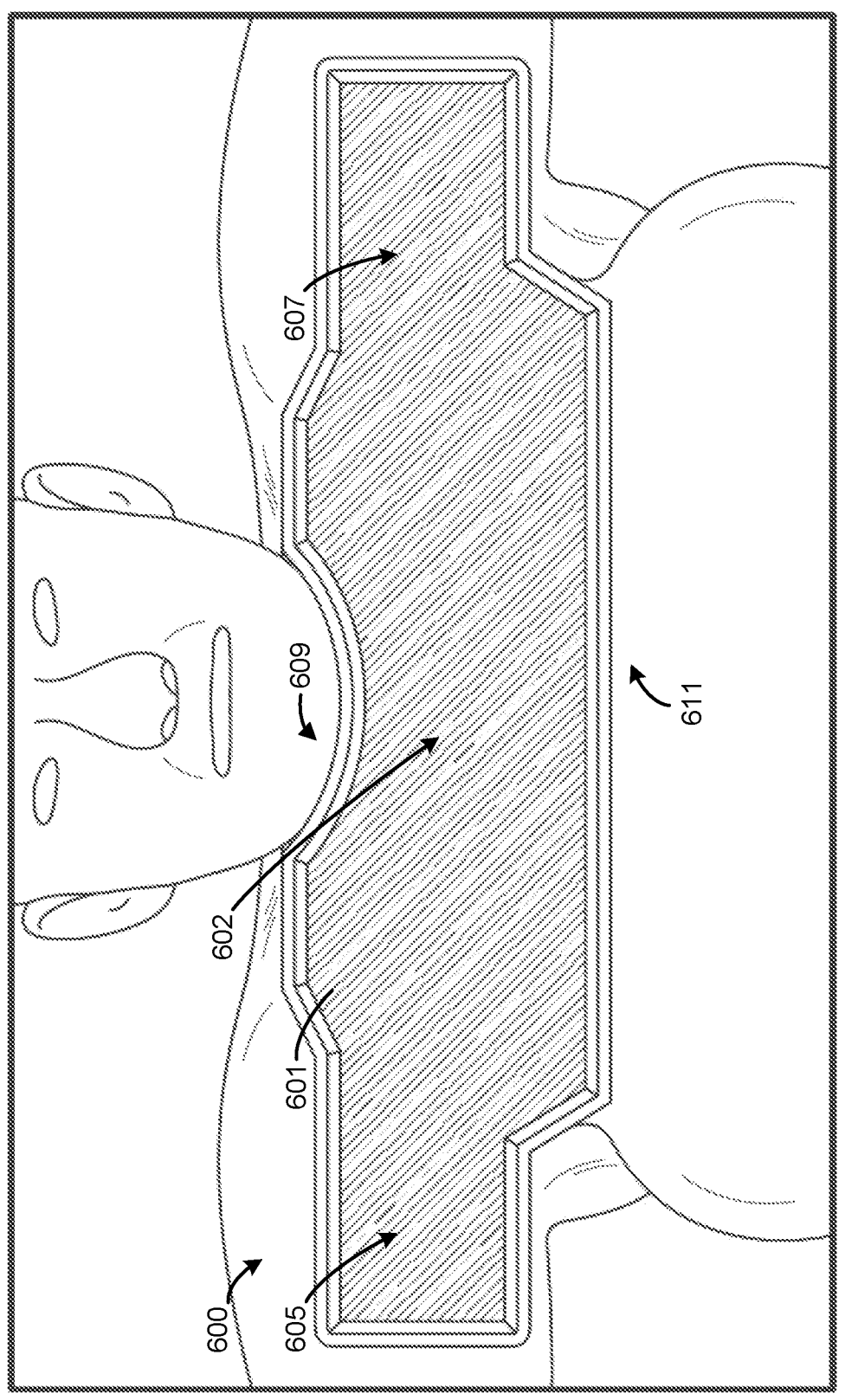

FIGS. 5-6 illustrate other example cervicothoracic mats 500, 600 which may include at least some of the same features and attributes as the cervicothoracic mats 100, 200 of FIGS. 1A-2B, as illustrated by the similar numbering, but with projections on the top surfaces 501, 601. For example, the cervicothoracic mats 500, 600 each have a top surface 501, 601 including a receiving portion 502, 602 and having projections, and an opposite bottom surface (see 103 of FIG. 1B). The top surface 501, 601 further includes a first lateral portion 505, 605 and a second lateral portion 507, 607 that respectively extend from the receiving portion 502, 602. Each cervicothoracic mat 500, 600 further includes a first peripheral portion 509, 609 and a second peripheral portion 511, 611. With cervicothoracic mat 500 of FIG. 5, the projections include fingerlike projections extending from the top surface 501. With cervicothoracic mat 600 of FIG. 6, the projections include cross-hatched projections extending from the top surface 601.

Figure 7:
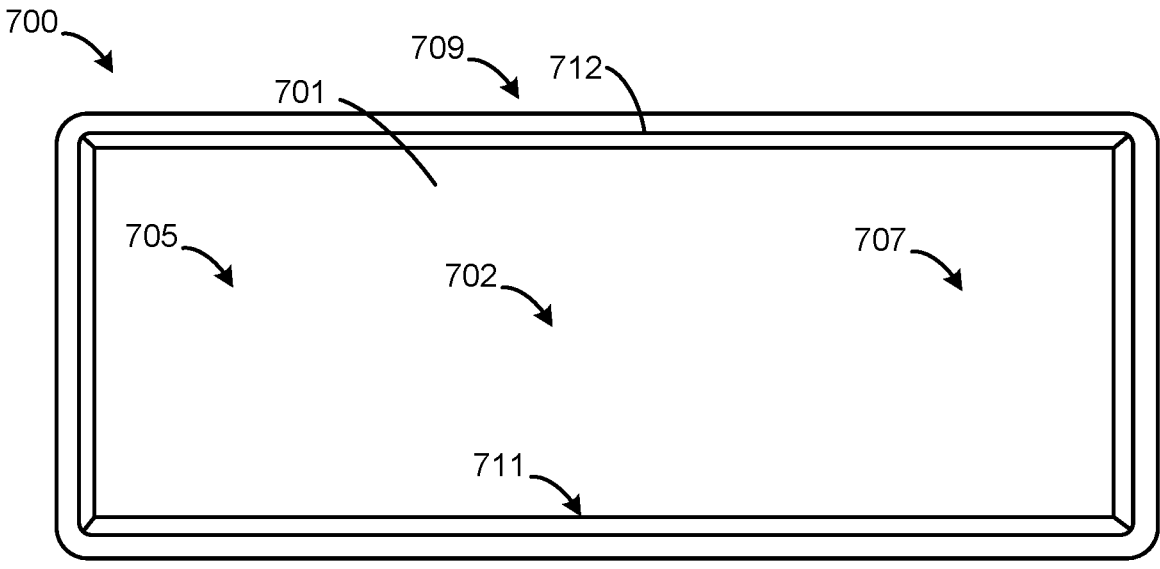
Figure 8:
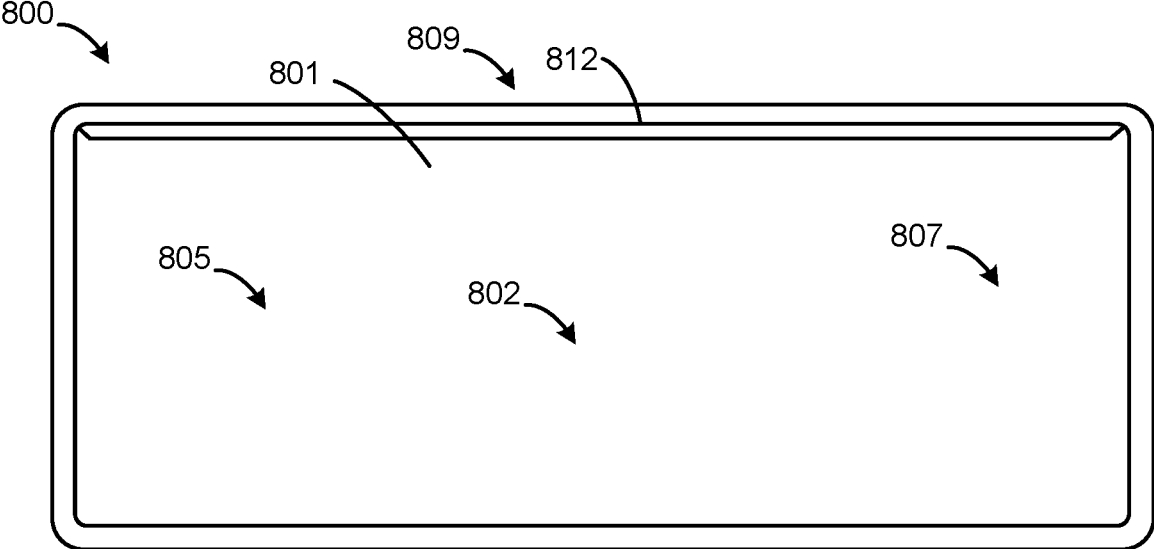

FIGS. 7-8 illustrate other example cervicothoracic mats 700, 800 which may include at least some of the same features and attributes as the cervicothoracic mats 100, 200 of FIGS. 1A-2B, as illustrated by the similar numbering, but with the cervicothoracic mats 700, 800 being rectangular in shape. For example, each cervicothoracic mat 700, 800 has a top surface 701, 801 including a receiving portion 702, 802 and an opposite bottom surface (see 103 of FIG. 1B). The top surface 701, 801 further includes a first lateral portion 705, 805 and a second lateral portion 707, 807 that respectively extend from the receiving portion 702, 802. Each cervicothoracic mat 700, 800 further includes at least a first peripheral portion 709, 809 and optionally a second peripheral portion 711. With cervicothoracic mat 700 of FIG. 7, the first and second peripheral portions 709, 711 include a ridge 712 that extends around the entire perimeter of the top surface 701. With cervicothoracic mat 800 of FIG. 8, the first peripheral portion 809 is a ridge 812 on one side of the perimeter of the top surface 701, such as a side configured to be arranged proximate to a chin or other surface of the patient which the surgeon would like to protect from sharp objects.

Figure 9:
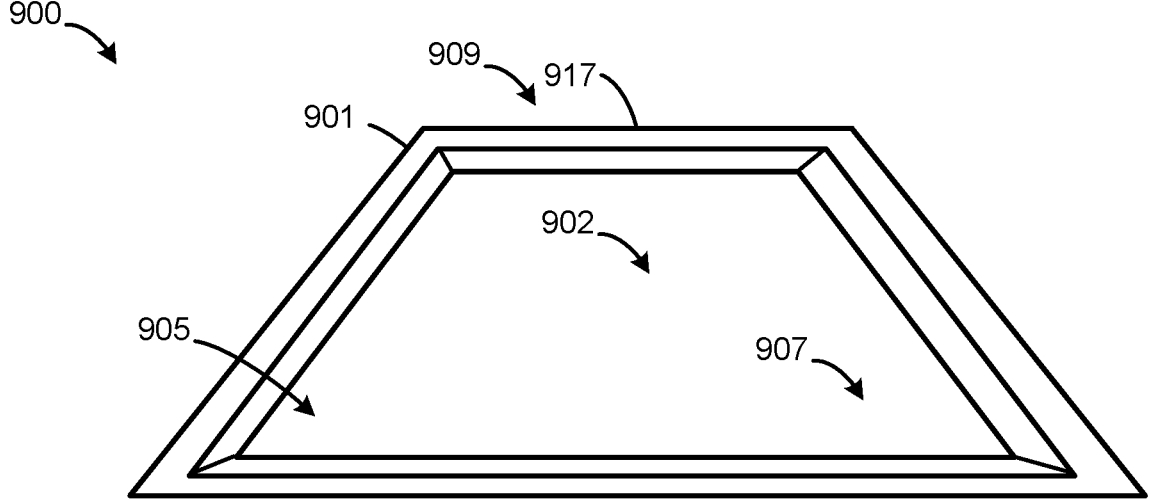

Examples are not limited to cervicothoracic mats shaped as illustrated by FIGS. 1-8. For example, FIG. 9 illustrates an example cervicothoracic mat 900 which may include at least some of the same features and attributes as the cervicothoracic mats 100, 200 of FIGS. 1A-2B, as illustrated by the similar numbering, but with the cervicothoracic mat 900 being in a trapezoid shape. The cervicothoracic mat 900 has a top surface 901 including a receiving portion 902 and an opposite bottom surface (see 103 of FIG. 1B). The top surface 901 further includes a first lateral portion 905 and a second lateral portion 907. The cervicothoracic mat 900 further includes at least a first peripheral portion 909 that includes a ridge 917.

The cervicothoracic mats may be formed in a variety of additionally non-illustrated shapes, such as non-geometric shapes, circles or ovals, diamond, stars, donut, and other shapes, and may include a variety of dimensions.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A cervicothoracic mat comprising:
   a top surface including a receiving portion configured to receive surgical instruments;
   an opposite bottom surface configured to contact a patient;
   a first lateral portion of the top surface extending from the receiving portion generally orthogonal from the receiving portion;
   a second lateral portion of the top surface extending from the receiving portion and generally orthogonal from the receiving portion;
   a first peripheral portion arranged along the perimeter of the cervicothoracic mat proximate to at least a first sub-portion of the receiving portion, the first peripheral portion including a recessed sub-portion, wherein the first peripheral portion is configured to receive the chin of the patient and the recessed sub-portion is configured to conform to the chin of the patient and to cover at least a portion of the chin of the patient; and
   a second peripheral portion arranged along the perimeter of the cervicothoracic mat and proximate to at least a second sub-portion of the receiving portion, the second peripheral portion being maintained in a non-planar configuration and configured to prevent surgical instruments from falling off of the patient, wherein the first peripheral portion and the second peripheral portion include a ridge that extends around the whole perimeter of the top surface of the cervicothoracic mat, the ridge being maintained in a non-planar configuration and configured to prevent surgical instruments from falling off of the patient, the recessed sub-portion extending from and being recessed from a portion of the ridge, and the cervicothoracic mat being comprised of silicon, and wherein the ridge that extends around the whole perimeter of the top surface of the cervicothoracic mat extends from the top surface in a direction away from the bottom surface and with a height in a range of 2 inches to ¼ inch, and is formed of silicon.

2. The cervicothoracic mat of claim 1, wherein the ridge includes a chin curve sub-portion arranged to receive the chin of the patient.

3. The cervicothoracic mat of claim 2, wherein the ridge includes angled sub-portions connecting the chin curve sub-portion to the first lateral portion and the second lateral portion.

4. The cervicothoracic mat of claim 1, wherein the second peripheral portion has a greater length relative to the first peripheral portion.

5. The cervicothoracic mat of claim 1, wherein at least the receiving portion includes a plurality of fingerlike projections extending therefrom.

6. The cervicothoracic mat of claim 1, wherein at least the receiving portion includes a plurality of cross-hatched projections extending therefrom.

7. The cervicothoracic mat of claim 1, wherein at least a sub-portion of the first peripheral portion is recessed relative to the first lateral portion and the second lateral portion.

8. The cervicothoracic mat of claim 1, wherein the first lateral portion and the second lateral portion are configured to extend toward a respective elbow of the patient.

9. The cervicothoracic mat of claim 1, wherein the second peripheral portion includes angled sub-portions connecting the first lateral portion and the second lateral portion.

10. The cervicothoracic mat of claim 1, wherein at least a sub-portion of the second peripheral portion is generally parallel to at least a sub-portion of the first peripheral portion.

11. The cervicothoracic mat of claim 1, wherein the second peripheral portion includes a portion of the top surface configured to extend over a length of the chest of the patient.

12. The cervicothoracic mat of claim 1, wherein the second peripheral portion is a projection of the top surface of the cervicothoracic mat configured to extend toward a midline of the thoracic region of the patient.

13. A cervicothoracic mat, comprising:
   a top surface including a receiving portion configured to receive surgical instruments;
   an opposite bottom surface configured to contact a patient;

a first lateral portion of the top surface extending from the receiving portion generally orthogonal from the receiving portion;

a second lateral portion of the top surface extending from the receiving portion and generally orthogonal from the receiving portion; and a peripheral portion arranged along the perimeter of the cervicothoracic mat proximate to the receiving portion, the peripheral portion including a ridge that extends along the whole perimeter of the cervicothoracic mat and including a recessed sub-portion which extends from and is recessed from a portion of the ridge, wherein the ridge is maintained in a non-planar configuration and is configured to prevent surgical instruments from falling off of the patient and extends around the whole perimeter of the top surface of the cervicothoracic mat and extends from the top surface in a direction away from the bottom surface and with a height in a range of 2 inches to ¼ inch, wherein the cervicothoracic mat including the ridge is comprised of silicon, and wherein the peripheral portion is configured to receive the chin of the patient and the recessed sub-portion is configured to conform to the chin of the patient and to cover at least a portion of the chin of the patient.

14. The cervicothoracic mat of claim 13, wherein the ridge extends from the top surface in a direction away from the bottom surface and is formed of silicon and the recessed sub-portion is configured to conform to the chin of the patient.

15. The cervicothoracic mat of claim 13, wherein the first lateral portion and the second lateral portion are configured to cover a respective portion of the chest of the patient.

16. The cervicothoracic mat of claim 13, wherein the receiving portion includes a recessed area disposed between the first lateral portion and the second lateral portion.

17. The cervicothoracic mat of claim 13, wherein the ridge is formed by additional silicon material formed along the whole perimeter at where the top surface and the bottom surface meet.

18. The cervicothoracic mat of claim 13, wherein the cervicothoracic mat is sterilizable.

* * * * *